(12) United States Patent
Sætre et al.

(10) Patent No.: US 6,488,629 B1
(45) Date of Patent: Dec. 3, 2002

(54) ULTRASOUND IMAGE ACQUISITION WITH SYNCHRONIZED REFERENCE IMAGE

(75) Inventors: Dagfinn Sætre, Horten (NO); Arve Stavø, Trondheim (NO); Vidar Lundberg, Trondheim (NO)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/918,866

(22) Filed: Jul. 31, 2001

(51) Int. Cl.[7] .................................................. A61B 8/00
(52) U.S. Cl. ........................................................ 600/443
(58) Field of Search ................................. 600/407–472; 367/7, 11, 130, 138; 73/625, 626; 128/916

(56) References Cited

U.S. PATENT DOCUMENTS

| | | | | |
|---|---|---|---|---|
| 5,477,858 A | * | 12/1995 | Norris et al. | 333/138 |
| 5,622,174 A | * | 4/1997 | Yamazaki | 600/441 |
| 5,669,387 A | * | 9/1997 | Mine | 600/441 |
| 5,701,897 A | * | 12/1997 | Sano | 600/451 |
| 5,766,129 A | * | 6/1998 | Mochizuki | 128/916 |
| 5,797,849 A | * | 8/1998 | Vesely et al. | 600/461 |
| 5,860,927 A | * | 1/1999 | Sakaguchi et al. | 600/453 |
| 6,246,898 B1 | * | 6/2001 | Vesely et al. | 600/424 |
| 6,397,098 B1 | * | 5/2002 | Uber et al. | 600/431 |
| 6,436,039 B1 | * | 8/2002 | Lannutti et al. | 600/437 |

* cited by examiner

Primary Examiner—Marvin M. Lateef
Assistant Examiner—Ali M. Imam
(74) Attorney, Agent, or Firm—Ostrager Chong & Flaherty LLP

(57) ABSTRACT

A system and a method for guiding and helping an ultrasound scanner user to acquire the correct projection/cut-plane when acquiring images of a physiological structure for comparison with previously acquired images. The ultrasound scanner screen area is divided in two parts, where one part is showing a reference image loop and the other part is showing the live image loop. The correct reference image loop is automatically retrieved from the image frame memory based on which cell in the stress protocol is active. The reference image loop is cycled with a speed which is automatically set by the software based on the current heart rate given by the live ECG acquisition. The display of the reference loop is "reset" (starting from the first image in the loop) at QRS trigger detection from the live ECG signal.

22 Claims, 5 Drawing Sheets

|  | 4-ch | 2-ch | PLAX | PSAX |
|---|---|---|---|---|
| REST | 1 | 2 | 3 | 4 |
| LOW DOSE | 5 | 6 | 7 | 8 |
| PEAK DOSE | 9 | 10 | 11 | 12 |
| RECOVERY | 13 | 14 | 15 | 16 |

REFERENCE LOOP    LIVE IMAGE

ULTRASOUND IMAGE ACQUISITION WITH SYNCHRONIZED REFERENCE IMAGE

BACKGROUND OF THE INVENTION

This invention relates to ultrasonic diagnostic imaging systems and, in particular, to the use of an ultrasonic imaging systems to acquire image loops of a patient body part.

One of the advantages of diagnostic ultrasound imaging is that it enables the production of real-time images. This capability is especially advantageous in the context of echocardiography, which studies the physiology of an organ, i.e., the heart, which moves incessantly. In contrast, real-time imaging is not necessary for abdominal and obstetrical ultrasound examinations because the tissues and organs being studied are substantially stationary or very slow moving, allowing the use of static imaging.

Electrical activity of the heart generates an electrical potential on the body surface. At any given location on the body, this potential includes contributions from every region of the heart, with the contribution from a particular region being inversely proportional to the square of the distance from the region to the location on the body. Given the anatomy of the heart and chest, the potentials at most locations on the body surface represent summed electrical activity from a large region of the heart.

The body surface electrocardiogram (ECG) is a measure of electrical activity of the heart. The ECG provides a measure of the potential difference between two points on the body surface as a continuous function of time. The ECG is routinely measured using standard ECG electrodes. In ultrasound, three electrodes are commonly used to record ECG signals.

Once the electrodes have been applied to the torso, the patient's heart can be stressed physiologically using a controlled protocol. The protocol may consist either of exercise or of pharmacological stress testing. For example, the patient may be exercised using a treadmill. Alternatives to the treadmill, such as climbing and bicycle ergometers, also may be used. In general, the stress protocol may have several stages, including control and warm-up stages, stages featuring progressively heavier stress, a relaxation stage, and a recording stage occurring between fifteen minutes and twenty-four hours after the test. Recording of ECG signals may take place during any or all of these stages.

Typically, an echocardiologist makes records of his/her ultrasound examinations for use in subsequent study and diagnosis. When an ultrasound stress examination is performed, image loops from different stress levels are acquired. An image loop is a sequence of images from one or more cardiac cycles that can be played back with endless repetition. It is important that the acquired image loops from the different stress levels be from the same projections or cut-planes of the heart, as diagnosis is based upon comparison of image loops taken from the same cross section of the heart at different stress levels.

Also in other applications of ultrasound it can be useful to compare a stored image loop with a live acquisition image in order to ensure that the newly acquired images to be compared with stored images have been acquired with the same probe position and same scan plane.

SUMMARY OF THE INVENTION

The present invention is directed to a system and a method for guiding and helping the ultrasound scanner user to acquire the correct projection/cut-plane when acquiring images of a physiological structure for comparison with previously acquired images. In accordance with the preferred embodiment of the invention, the ultrasound scanner screen area is divided in two parts, where one part is showing a reference image loop and the other part is showing the live image loop. More than one reference image loop may be shown, e.g., stress echo reference image loops both from a baseline and a previous stress level may be shown in a three-image screen layout.

The reference image loop is synchronized with the live imaging based on the patient's ECG signal. Alternatively, some other physiological signal that varies in synchrony with the heart beat could be used, such as blood pressure, Doppler signal, a frame correlation coefficient, or even the average gray-scale from a region of interest in the image itself. The period (repetition time) of the loop is predicted using previous cardiac cycle(s).

The reference image loop in a stress examination will typically show the baseline and/or previous stress level(s), and the reference image will be automatically updated to the correct projection/cut-plane as the user is going through a protocol examination. A protocol is a predefined sequence of image acquisitions. In a stress examination the protocol defines both the projections/ cut-planes and the stress levels used in the examination in a two-dimensional matrix of images.

An essential and difficult part of ultrasound imaging is the process of finding the probe position and scan plane that gives the best possible image. When comparing images from different image acquisitions, it is important to be able to obtain the same projections (same probe position and same scan plane). The present invention makes the process easier as it provides the user with a live comparison option that can be selected during image acquisition. While acquiring images, the user can see in real time that he is aligning correctly according to the reference image loop that is used for comparison.

In a stress examination the user will be able to acquire the images faster and with better accuracy using this new technique. Using the reference image loop will make it easier to acquire the corresponding projections, thereby reducing the risk of comparing slightly different projections. If the image loops at two different stress levels are acquired at slightly different angles, there will be a risk that wall motion changes from one stress level to another will be interpreted wrongly.

Also in a stress examination, the invention gives additional information with respect to what happens to the patient during the examination, as the state of the heart at the different stress levels can be compared directly as the examination is in progress.

In accordance with the preferred embodiment of the invention, the algorithm for displaying a reference loop image in response to selection of a reference image loop display option by the system operator is implemented in software. The correct reference image loop is automatically retrieved from the image frame memory, i.e., cine memory, based on which cell in the stress protocol is active. The reference image loop is cycled with a speed that is automatically set by the software based on the current heart rate given by the live ECG acquisition. The display of the reference loop is "reset" (starting from the first image in the loop) at QRS trigger detection from the live EGG signal or based on a corresponding point in some other signal.

Other aspects of the invention are disclosed and claimed below.

DETAILED DESCRIPTION OF THE PREFERRED EMBODIMENTS

Figure 1:
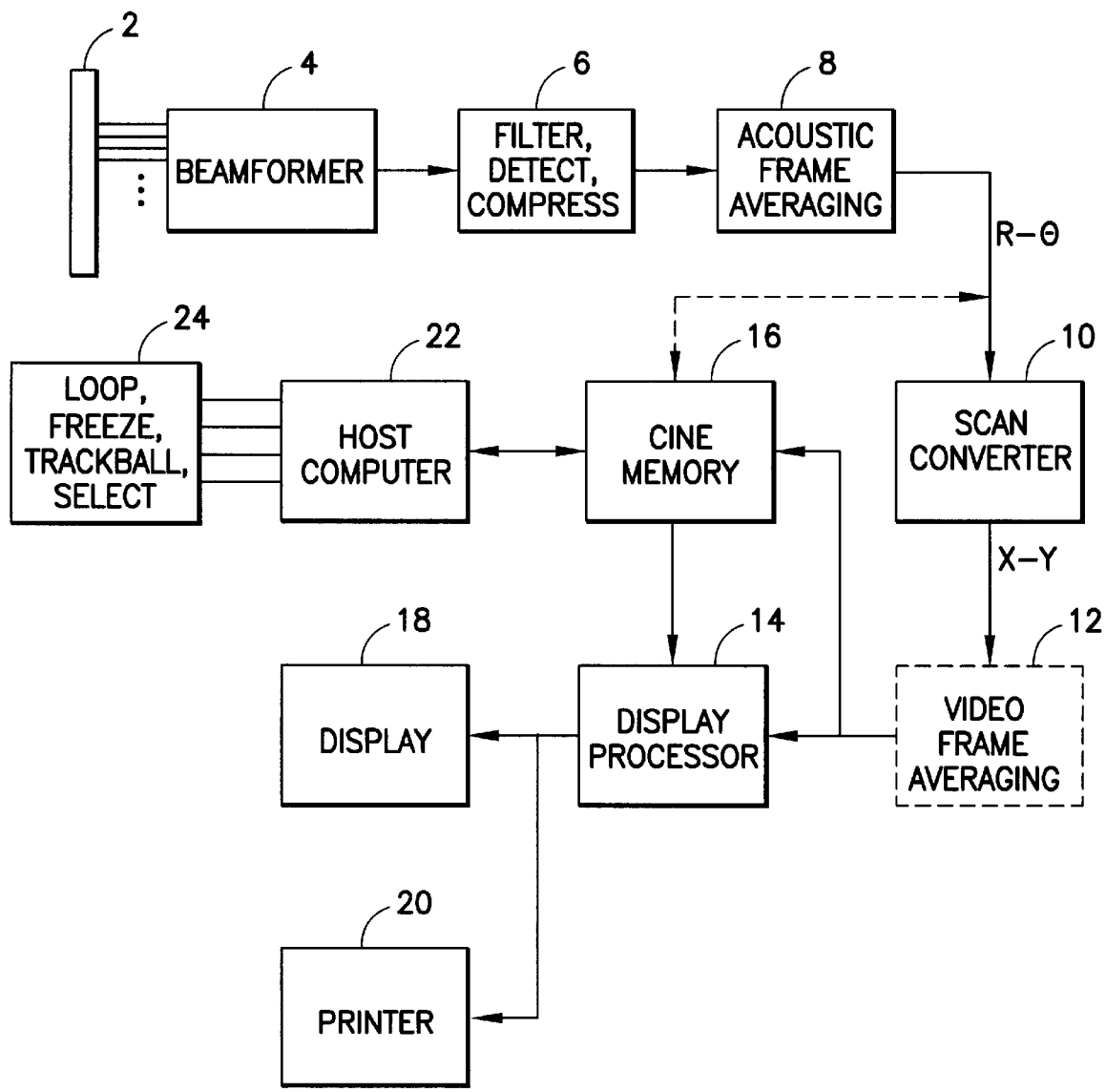
FIG. 1 is a block diagram of a typical ultrasound imaging system.

The basic signal processing chain for one type (B-mode imaging) of conventional ultrasound imaging system is depicted in FIG. 1. However, it should be appreciated that the present invention can be employed in conjunction with other scanning modes (e.g., TVI).

Referring to FIG. 1, an ultrasound transducer array 2 is activated to transmit an acoustic burst along a scan line. The returned RF signals are detected by the transducer elements and then formed into a receive beam by the beamformer 4. The beamformer output data (I/Q or RF) for each scan line is passed through a processing chain 6 which, for the B-mode, includes equalization filtering, envelope detection and logarithmic compression. Depending on the scan geometry, up to a few hundred vectors may be used to form a single acoustic image frame. To smooth the temporal transition from one acoustic frame to the next, some acoustic frame averaging 8 may be performed before scan conversion. The frame averaging may be implemented by an FIR or an IIR filter in general, the compressed images are in R-θ format (for a sector scan), which is converted by the scan converter 10 into X-Y format for video display. On some systems, frame averaging may be performed on the video X-Y data (indicated by dashed block 12) rather than the acoustic frames before scan conversion, and sometimes duplicate video frames may be inserted between acoustic frames in order to achieve a given video display frame rate. The video frames are passed on to a display processor 14, which basically maps the video data to a gray map for video display on a display monitor 18. A gray-mapped image frame from display processor 14 can also be printed out on a printer 20.

System control is centered in a host computer 22, which accepts operator inputs through an operator interface 24 (e.g., a control panel) and in turn controls and synchronizes the various subsystems, e.g., the beamformer. (In FIG. 1, only the image data transfer paths are depicted.) During B-mode imaging, a long sequence of the most recent images are stored and continuously updated automatically in a cine memory 16. Some systems are designed to save the R-θ acoustic images (this data path is indicated by the dashed line in FIG. 1), while other systems store the X-Y video images. The image loop stored in cine memory 16 can be reviewed via trackball control, and a section of the image loop can be selected for hard disk storage. For an ultrasound scanner with free-hand three-dimensional imaging capability, the selected image sequence stored in cine memory 16 is transferred to the host computer 22 for three-dimensional reconstruction. The result is written back into another portion of the cine memory, from where it is sent to the display system 18 via display processor 14. In addition, the host computer 22 may be programmed to control various operating parameters as a function of the current frame (or latest sequence of frames) of video X-Y data. This is accomplished by freezing the current image frame of data via the user control panel, analyzing the data and then setting the appropriate system parameters in accordance with an adaptive algorithm. When adaptive parameter optimization is complete, the user unfreezes the display via the control panel 24.

The functions of the host computer 22, processor 6 and scan converter 10 can be performed by the same computer.

Figure 2:
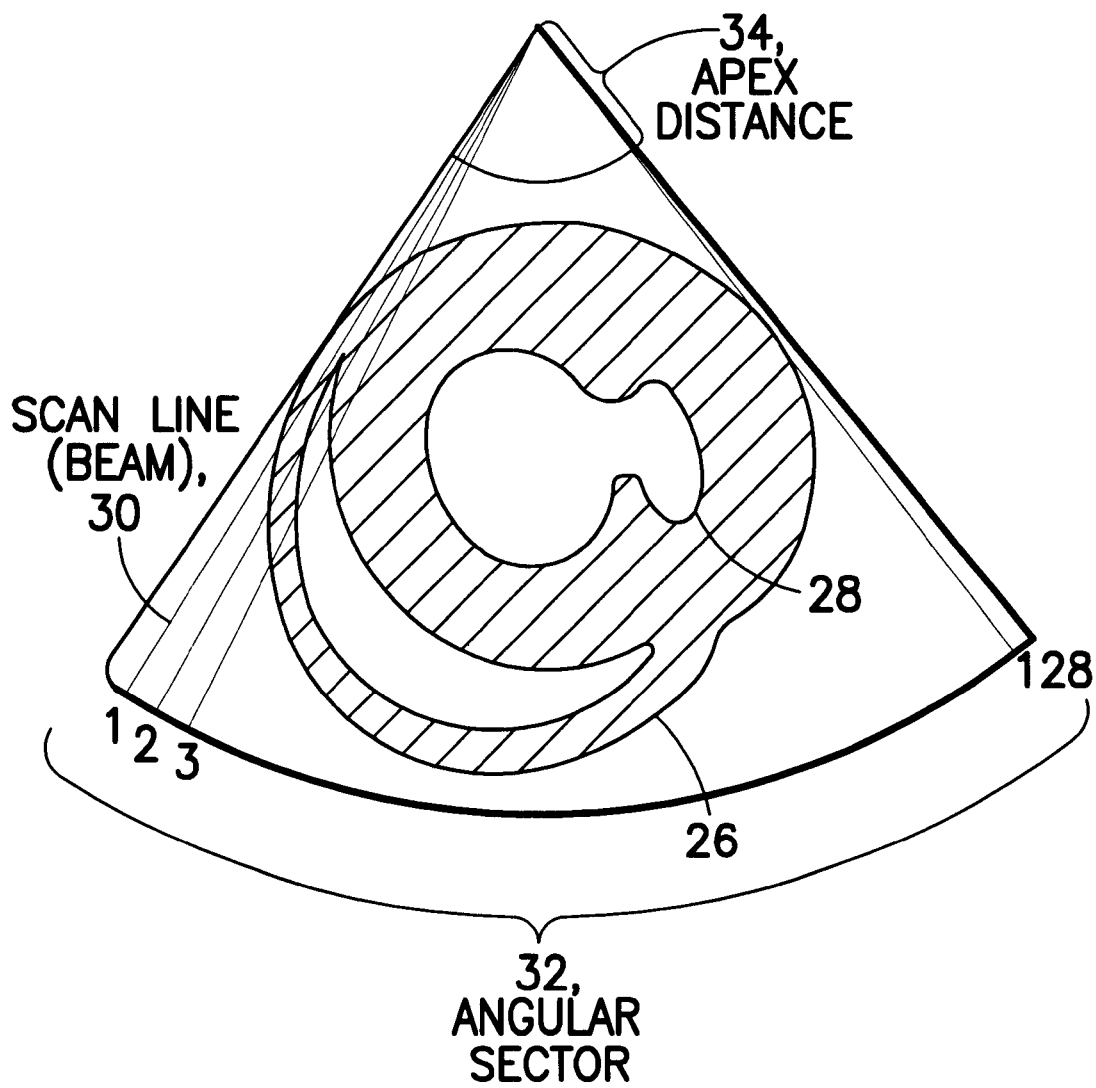
FIG. 2 is a drawing showing a sample sector scan image of an anatomical structure.

The system shown in FIG. 1 (and other systems not shown) can be used to perform an ultrasound stress examination. FIG. 2 shows a typical ultrasound sector scan image of an anatomical structure 26, for example, a heart. Feature 28 is an outline of a heart chamber. The image is obtained using a conventional transducer which forms a plurality of scan lines or beams 30 that traverse an angular sector 32 in a plane. There are typically 128 or more scan lines 30 per image in the example of FIG. 2. The scan line data are processed by an ultrasound image processor and viewed on a display monitor as a succession of image frames, in a conventional manner. The image formed by each successive pass through the angular sector 32 (e.g., 128 scan lines in the example of FIG. 2) defines one image frame. The "image frame rate" of an ultrasound device is the number of image frames obtained per unit time. A typical frame rate may range from 25 to 60 frames per second (FPS). The "image frame period" is the amount of time between adjacent frames. In FIG. 2, reference numeral 34 indicates the scanning parameter "apex distance", which is the distance from the transducer's transmitter emission point to the region of the image where data collection begins. The dots along scan line 128 represent scan line data points. Each data point ultimately represents a pixel value on the display monitor. For the purpose of illustration, fourteen data points are shown along the 128th scan line. A typical scan line 30 actually may have 300–400 data points.

The present invention is used for imaging anatomical structures that exhibit periodic physiological motion wherein the motion defines successive periodic cycles. The heart and lungs are examples of anatomical structures that have periodic cycles. Since the heart cycle (cardiac cycle) is used to illustrate certain features of the present invention, some background on the heart cycle is provided to further understand the invention.

Figure 3:
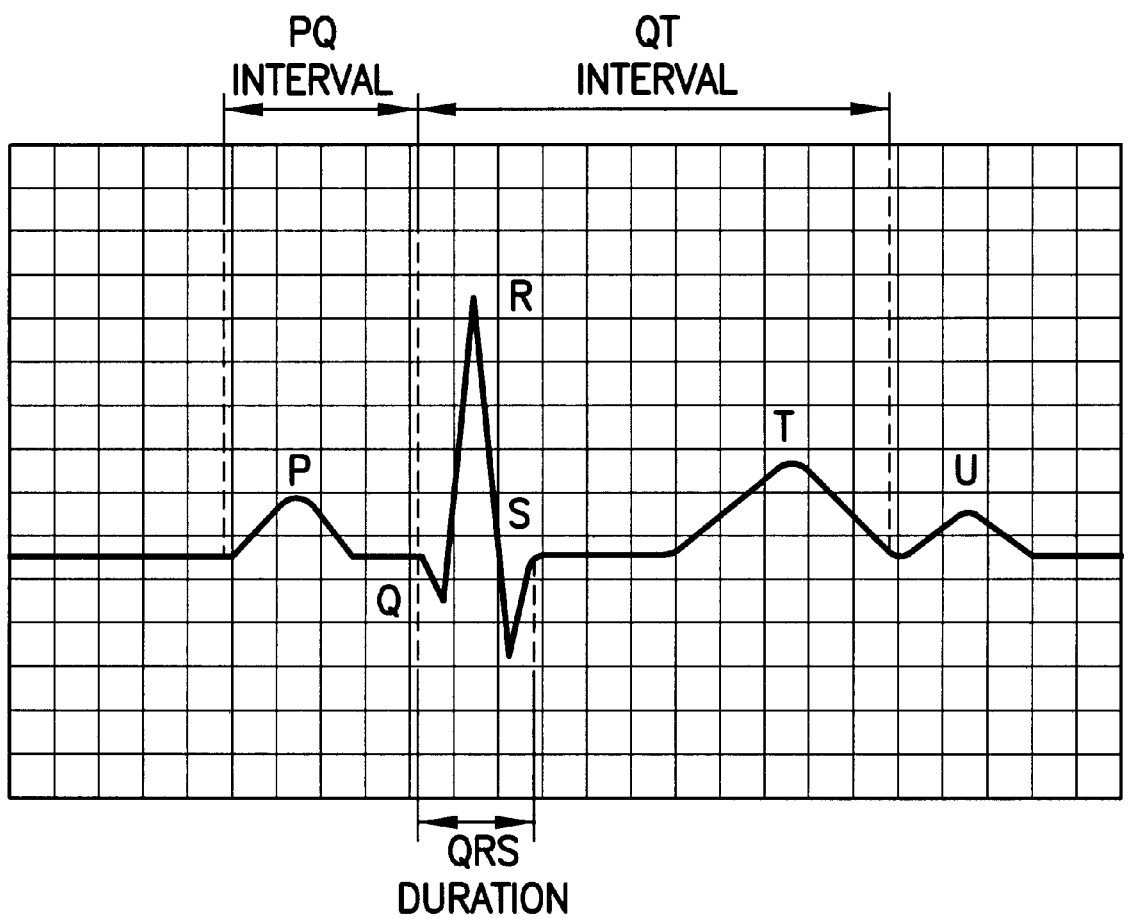
FIG. 3 is a drawing showing the shape of a typical EGG waveform.

FIG. 3 shows the shape of a typical ECG waveform acquired from a human heart. The ECG is a scalar representation that shows deflections resulting from atrial and ventricular activity as changes in the magnitude of voltage and polarity with time. The deflections are referred to as "waves." For example, the first deflection is the P wave. One particular point of interest of the ECG is the QRS interval or QRS complex, and particularly the peak of the R wave, also referred to as the QRS trigger. The heart cycle is defined as the period from the beginning of one heart beat to the beginning of the next heart beat. The heart cycle has two important time intervals during each cycle, namely the systole and diastole. During diastole, the left ventricle fills with blood. During systole, the left ventricle contracts to pump the blood out of the heart. During systole, there is a large amount of motion in the anatomical parts of the heart, whereas there is relatively less motion during diastole. Diagnostic heart studies are often concerned with the action of anatomical structures during systole. The QRS trigger provides a convenient way to detect the onset of systole and is often used in the present invention to control the ultrasound scanner for capturing image data and displaying reference image loops.

The ultrasound imaging system in accordance with the preferred embodiment of the present invention has a cine memory 16 (see FIG. 1) or other image frame memory for collecting and storing image data. The image data may be stored as raw data representing the pixels obtained from data points along each scan line 30 shown in FIG. 2, or the image data may be stored as processed frame data, in the same manner as a frame of video. The imaging data is preferably stored and packaged or formatted as image loops. Each image loop includes frame data representing a plurality of image frames acquired at spaced time intervals within a physiologic (e.g., heart) cycle. Preferably each image loop includes a loop header and the frame data for one physiologic cycle. The image frame data is packaged as a plurality of frame packets. The loop header is used to identify the loop by number, for example, a cycle number in a stream of collected data.

Consider an example wherein the anatomical structure is the heart, the physiologic cycle is the heart cycle, and the image loop includes a plurality of image frames acquired for one physiologic cycle at a predefined time relative to a QRS trigger. For example, the image frames may be acquired from one QRS trigger to the next, or from a few milliseconds after the QRS trigger to a few milliseconds after the next QRS trigger. If the frame rate of the acquisition equipment is 30 FPS and the heart cycle is about one second, then there will be about 30 frame packets in each image loop. Each frame packet preferably includes a frame header and the scan line data associated with the frame. The scan line data is preferably packaged as a plurality of scan line packets. The frame header identifies the frame by number, for example, the frame number in a sequence of frame packets. The frame numbers may begin with zero. In the he art cycle example, frame zero would be acquired at the QRS trigger or a predetermined time period thereafter. Each scan line packet includes a scan line header and the individual line data associated with the scan line. The scan line header comprises a line number representing a position within a scan sector, such as the last scan line shown in FIG. 2 (scan line 128). The individual line data represents the data points along the scan line.

The image loop header, the frame header and the scan line header function as an identification portion or ID tag of a data packet in a digital image communication scheme. These headers may also be used to store additional information to assist in processing the image data. For example, the loop header may include the following: (1) timing of the image loop with respect to a known point of the physiological cycle, such as the timing with respect to the QRS trigger; (2) time interval of the image loop (this may be used for playback control); (3) type of physiologic cycle (e.g., heart cycle, respiratory cycle); (4) geometric parameters of the ultrasound scan (e.g., apex distance, distance between data points, etc.); (5) number of frames or frame packets in the loop; (6) type of scan line data (e.g., B-mode data, color flow, harmonic mode); and (7) identification of during which cell of a stress protocol the image loop was acquired.

The frame header may include the time between adjacent, successively acquired or collected frames (i.e., current and previous frame). This information is particularly important w hen image frames are acquired or collected at different frame rates. During playback, this information is used to determine how long the frame should persist on the display screen before being replaced by the next frame. The frame header may also include the number of scan lines or scan line packets in the frame packet (i.e., scan line density).

In accordance with the preferred embodiment of the present invention, frame acquisition and concurrent display of a reference image loop are synchronized with the heart cycle using the QRS trigger point, wherein each image loop goes from one QRS trigger point (or a predetermined time with respect to the QRS trigger point) to the next QRS trigger point. More generally, an image loop, as defined herein, starts at a first predefined time with respect to a predetermined event in a physiologic cycle and ends at a second predefined time with respect to the predetermined event in the physiologic cycle. In one preferred scheme, the image loop has a length of one physiologic cycle.

As previously noted, the image frame data stored in the image loops may represent raw image data before it is processed by the scan converter 10 (see dashed line in FIG. 1), or the image frame data may represent display-type pixel data (i.e., raw image data which was processed by the scan converter). Data is typically acquired at the highest image frame rate necessary to fully capture the motion of the fastest-moving structures presumed to be present. For a fast-moving structure such as the heart, an acquisition frame rate of more than 30 FPS must be used to accurately represent the motion during the fastest portion of the heart cycle.

The present invention is directed to a system and a method for guiding and helping the ultrasound scanner user to acquire the correct projection/cut-plane when acquiring images of a physiological structure for comparison with previously acquired images. In accordance with the preferred embodiment of the invention, the ultrasound scanner screen area is divided in two parts, where one part is showing a reference image loop and the other part is showing the live image loop. Alternatively, more than one reference image loop may be shown, e.g., stress echo reference image loops both from a baseline and a previous stress level may be shown in a three-image screen layout.

In accordance with the preferred embodiment of the invention, the reference image loop is synchronized with the live imaging based on the patient's ECG signal. The period (repetition time) of the loop is predicted using previous cardiac cycle(s). The reference image loop in a stress examination will typically show the baseline and/or previous stress level(s), and the reference image will be automatically updated to the correct projection/cut-plane as the user is going through a protocol examination.

In accordance with the preferred embodiments of the present invention, the system operator may select (using a keyboard, a graphical user interface or other operator interface) a live comparison option during image acquisition. When the live comparison option is activated, the system operator is provided with a visual display of a reference image loop, which the system operator compares to the live images currently being acquired. During the live image acquisition, the system operator compares the cycling reference images with the cycling live images, adjusting the position of the probe until he/she is satisfied that the visual resemblance of the reference and live image loops is sufficiently close, indicating that the current probe position is substantially the same as when the reference image loop was acquired.

Figure 4:
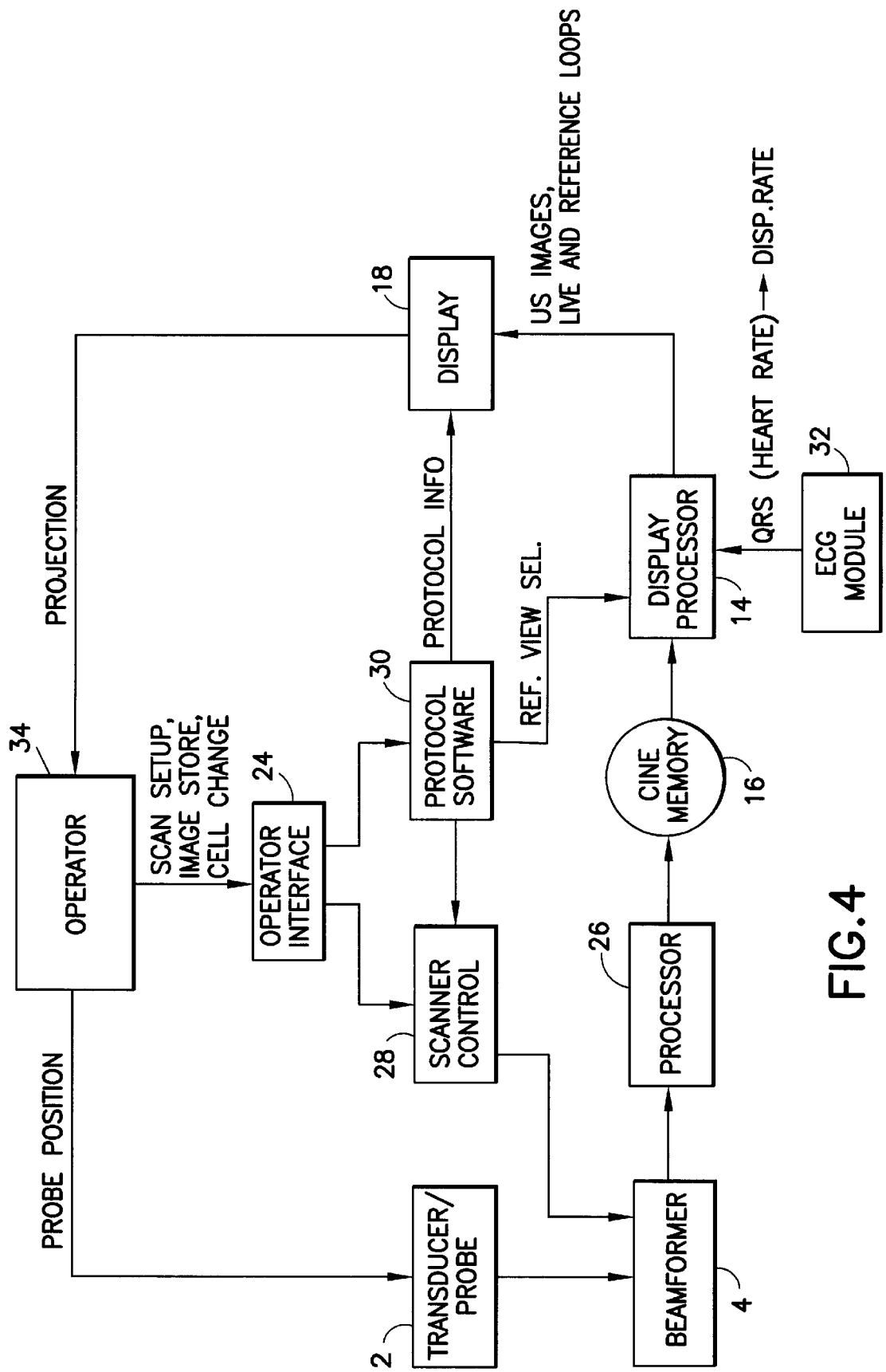
FIG. 4 is a block diagram of a diagnostic ultrasound imaging system in accordance with the preferred embodiment of the present invention.

FIG. 4 is a block diagram of a medical ultrasound imaging system in accordance with the preferred embodiment of the invention. The image frame acquisition subsystem comprises a transducer probe 2, a transmit/receive beamformer 4, and an image processor 26. During a stress protocol examination, the transducer probe 2 is directed toward the heart of a patient. The beamformer 4 is operated under control of a scanner controller 28 responsive to commands input by a human operator 34 via an operator interface 24. A complete scan is performed by acquiring a series of echoes in which the transmit beamformer is gated ON momentarily to energize each transducer element, and the subsequent echo signals produced by each transducer element are applied to the receive beamformer, which applies respective beamforming time delays to the received signals and then combines the time-delayed signals to produce a single summed echo signal. This process is repeated for each scan line until an entire frame has been acquired. Each frame of image data is stored in the cine memory 16 and sent to the display processor 14. The display processor 14 maps the image data for display and sends the mapped image frames to the display monitor 18.

Figures 5, 6:
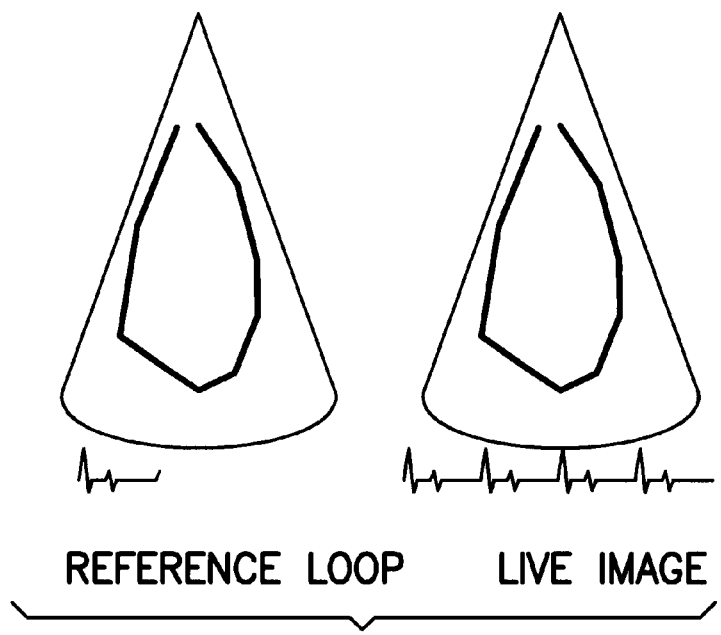
FIG. 5 is a drawing showing a graphical display for indicating the current state of a stress protocol examination. The image loops are normally acquired in the order indicated by the numbering of the cells in the protocol. In the exemplary state depicted in FIG. 5, the first four cells are filled and the fifth cell is "active", meaning that the image loop for that cell will be the next image loop acquired.
FIG. 6 is a drawing showing an example of an ultrasound scanner image display in accordance with the preferred embodiment of the present invention.

The ECG monitor 32 is coupled to the patient and monitors the patient's heart during a stress protocol examination. One example of a soft-key display of the state of an ongoing pharmacological stress protocol examination is depicted in FIG. 5. Each numbered field represents a respective cell of a stress protocol having four stages (rows): rest; low dose; peak dose; and recovery. The different projections or views are given in respective columns bearing the headings: 4-ch=4-chamber, 2-ch=2-chamber, PLAX=Parasternal Long Axis, PSAX=Parasternal Short Axis. These are some of the standard views (projections) used in cardiac ultrasound. Image loops are normally acquired as indicated by the numbering of the cells in the protocol. The dark shading indicates that these cells are filled, while the lightly shaded cell is the active cell. When the system operator starts image acquisition in accordance with the protocol, the system sets the active cell to the first cell in the protocol. The system operator will normally move to the next cell by storing an image loop into the active cell, but the active cell can also be changed by the system operator by pressing arrow keys (moving to the desired cell) on the operator interface 24. The keys may be virtual keys displayed on a graphical user interface.

In accordance with the preferred embodiment of the invention, the stress protocol software 30 monitors which cell is active and which cells have been filled, and outputs a Reference View Selection instruction which identifies the new cell when the active cell has been changed. In response to the Reference View Selection instruction, the display processor 14 retrieves the identified reference image loop from the cine memory and displays it. The display processor 14 also receives QRS trigger and heart rate data from the ECG monitor 32. The display processor 14 uses this information to determine the start time and to set a display frame rate for display of the selected loop of reference images.

As disclosed above, the reference image loop is loaded from cine memory. It might actually first be loaded from the hard disk into cine memory, and then displayed from cine memory.

As the operator conducts the stress protocol examination, the protocol software continually updates the display of the stress protocol cell matrix depicted in FIG. 5. If the active cell is at any of the stages following the first stage, a reference image (i.e., an image acquired in the previous stage for the same projection or view) can be shown together with the live image, as seen in FIG. 6. The reference image is taken from one of the previous stages for the same projection as that of the active cell. The live image loop accompanied by the live ECG are shown running on the right-hand side of the display monitor. The reference image loop (for one heart cycle) with corresponding ECG are shown running on the left-hand side. The image frames for the reference image loop are retrieved from the cine memory 16 by the display processor 14. The correct reference image loop is retrieved based on the Reference View Selection signal sent by the stress protocol software 30 concerning which cell is active. The reference image loop is cycled with a speed based on the current heart rate given by the live ECG acquisition. The display of the reference image loop is "reset" (starting from the first image in the loop) in response to detection by the display processor 14 of the QRS trigger in the live ECG waveform being output by the ECG monitor 32. The display processor concurrently outputs the reference and live image loops to the monitor 18. This concurrent display allows the system operator to compare the cycling reference images with the cycling live images, adjusting the position of the transducer probe 2 until he/she is satisfied that the visual resemblance of the reference and live image loops is sufficiently close, indicating that the current probe position is substantially the same as when the reference loop was acquired?

In accordance with the preferred method for live image acquisition with synchronized display of one or more reference image loops, the display speed of the reference image loop is updated every time the QRS trigger is detected in the live ECG signal. A new reference image loop is loaded when the system operator changes the active cell in the stress protocol. The active cell is normally changed due to an image store operation (i.e., storing a loop to the currently active cell automatically causes the next cell to be selected as active). The system operator must manually position the probe when the active cell has been changed. The scanner is programmed to guide the system operator by showing a reference image loop for the corresponding projection or view.

While the invention has been described with reference to preferred embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore it is intended that the invention not be limited to the particular embodiment disclosed as the best mode contemplated for carrying out this invention, but that the invention will include all embodiments falling within the scope of the appended claims.

What is claimed is:

1. A method for displaying images based on a physiologic cycle, comprising the following steps:

acquiring a first image loop comprising a first sequence of image frames along a first scan plane through a patient during a first time span;

storing said first image loop in memory;

continuously monitoring a physiologic cycle of said patient;

acquiring a second image loop comprising a second sequence of image frames along a second scan plane through said patient during a second time span subsequent to said first time span; and concurrently displaying said first and second image loops in dependence on a result of said continuous monitoring step.

2. The method as recited in claim 1, further comprising the steps of subjecting said patient to a first stress state during said first time span and to a second stress state different than said first stress state during said second time span.

3. The method as recited in claim 1, wherein said physiologic cycle is the cardiac cycle.

4. The method as recited in claim 3, wherein said result of said continuous monitoring step comprises detecting a QRS trigger for each cardiac cycle.

5. The method as recited in claim 1, further comprising the steps of visually comparing said displayed first and second image loops; and adjusting the position of a transducer probe relative to said patient if visually apparent differences between said displayed first and second image loops indicate that said first and second image loops were acquired along respective scan planes which are significantly different.

6. An imaging system comprising:

a monitor for continuously monitoring a physiologic cycle of a patient and outputting electrical signals representing characteristics of said physiologic cycle;

a transducer array comprising a multiplicity of transducer elements for transmitting wave energy in response to electrical activation and transducing returned wave energy into electrical signals;

a display monitor;

memory storing a reference image loop comprising a first sequence of image frames acquired along a scan plane through a patient; and a computer programmed to perform the following steps:
retrieving said reference image loop from said memory;
controlling said transducer array to acquire a live image loop comprising a second sequence of image frames during a second time span subsequent to said first time span; and
controlling said display monitor to concurrently display said first and second image loops in dependence on an output of said monitor.

7. The system as recited in claim 6, further comprising an operator interface and stress protocol software for determining which cell of a stress protocol is active based on information inputted via said operator interface.

8. The system as recited in claim 7, wherein said memory stores reference image loops for a plurality of different projections, and said computer is further programmed to retrieve the one of said plurality of reference image loops having a projection corresponding to a desired projection of said active cell.

9. The system as recited in claim 6, wherein said monitor comprises an ECG monitor.

10. The system as recited in claim 6, wherein said first and second image loops are displayed in synchronism starting at a time determined by a QRS trigger of said monitor output.

11. The system as recited in claim 10, wherein said monitor comprises an ECG monitor.

12. The system as recited in claim 11, wherein said first and second image loops are displayed in synchronism starting at a time determined by a QRS trigger of said monitor output.

13. A system for displaying images based on a physiologic cycle, comprising:

means for acquiring a first image loop comprising a first sequence of image frames along a first scan plane through a patient during a first time span;

memory for storing said first image loop;

a monitor for continuously monitoring a physiologic cycle of said patient;

means for acquiring a second image loop comprising a second sequence of image frames along a second scan plane through said patient during a second time span subsequent to said first time span; and means for concurrently displaying said first and second image loops in dependence on an output of said monitor.

14. The system as recited in claim 13, further comprising an operator interface and means for determining which cell of a stress protocol is active based on information inputted via said operator interface.

15. The system as recited in claim 14, wherein said memory stores reference image loops for a plurality of different projections, and said means for concurrently displaying comprises means for retrieving the one of said plurality of reference image loops having a projection corresponding to a desired projection of said active cell.

16. An imaging system programmed to concurrently display reference and live image loops in synchronism, wherein said reference image loop was acquired in a scan plane which corresponds to a desired scan plane for acquisition of said live image loop.

17. The imaging system as recited in claim 16, comprising a monitor for continuously monitoring a physiological cycle of a patient, wherein said reference and live image loops are displayed at a start time which is dependent on a characteristic of said physiological cycle acquired by said monitor.

18. The imaging system as recited in claim 17, wherein said monitor comprises an ECG monitor.

19. The imaging system as recited in claim 17, wherein said programming comprises display processor software which updates the speed of said reference image loop every time said characteristic of said physiologic cycle is detected by said monitor.

20. The imaging system as recited in claim 17, further comprising an operator interface, wherein said programming comprises stress protocol software which causes the next cell in a stress protocol to be selected in response to inputting via said operator interface of a predetermined command.

21. The imaging system as recited in claim 20, wherein said predetermined command is a store image command.

22. The imaging system as recited in claim 20, wherein said programming comprises display processor software which loads a next reference image loop in response to selection of said next cell.

* * * * *